US011076911B2

United States Patent
Kong et al.

(10) Patent No.: US 11,076,911 B2
(45) Date of Patent: Aug. 3, 2021

(54) APPLICATION OF RADIOFREQUENCY CATHETER ABLATION SYSTEM TO TREATMENT OF ESSENTIAL HYPERTENSION

(71) Applicant: NANJING KHONS MEDTECH CO., LTD., Jiangsu (CN)

(72) Inventors: Xiangqing Kong, Nanjing (CN); Younian Kong, Nanjing (CN)

(73) Assignee: NANJING KHONS MEDTECH CO., LTD., Nanjing (CN)

( * ) Notice: Subject to any disclaimer, the term of this patent is extended or adjusted under 35 U.S.C. 154(b) by 899 days.

(21) Appl. No.: 15/574,570

(22) PCT Filed: Jun. 24, 2016

(86) PCT No.: PCT/CN2016/087082
§ 371 (c)(1),
(2) Date: Nov. 16, 2017

(87) PCT Pub. No.: WO2017/101289
PCT Pub. Date: Jun. 22, 2017

(65) Prior Publication Data
US 2018/0125572 A1    May 10, 2018

(30) Foreign Application Priority Data
Dec. 17, 2015  (CN) .......................... 201510956065.8

(51) Int. Cl.
*A61B 18/14* (2006.01)
*A61B 8/12* (2006.01)
*A61B 18/00* (2006.01)

(52) U.S. Cl.
CPC ............ *A61B 18/1477* (2013.01); *A61B 8/12* (2013.01); *A61B 18/1492* (2013.01);
(Continued)

(58) Field of Classification Search
CPC ...... A61B 18/1477; A61B 2018/00511; A61B 18/1492
See application file for complete search history.

(56) References Cited

U.S. PATENT DOCUMENTS

2011/0118542 A1*  5/2011  Cucin ................. A61M 1/0058
                                                    600/104
2012/0029505 A1*  2/2012  Jenson ............... A61B 18/1492
                                                    606/34
(Continued)

*Primary Examiner* — Linda C Dvorak
*Assistant Examiner* — Ryan T Clark
(74) *Attorney, Agent, or Firm* — Oliff PLC

(57) ABSTRACT

An application of a radiofrequency catheter ablation system to treatment of essential hypertension. The treatment process is under ultrasonic guidance, an electrode needle is made to penetrate into target tissue of a patient, electrification is conducted to start ablation, the needle is withdrawn or made to penetrate into the other side of the target tissue for target ablation after reaching ablation temperature and duration time, and overall ablation treatment is completed. The system can treat a secondary center for regulating the activity of a whole-body sympathetic system to reduce its activity, thus, the blood pressure level of a patient can be reduced, and fewer kinds and smaller dosage of antihypertensive drugs taken or ceased altogether. By treating the secondary center, the activity of the whole-body sympathetic system, insulin resistance and whole-body fibrosis is reduced, and other diseases characterized in activity abnormity of the sympathetic system might be treated too.

20 Claims, 1 Drawing Sheet

(52) U.S. Cl.
CPC ............... *A61B 2018/00345* (2013.01); *A61B 2018/00434* (2013.01); *A61B 2018/00511* (2013.01); *A61B 2018/00577* (2013.01); *A61B 2018/00791* (2013.01)

(56) References Cited

U.S. PATENT DOCUMENTS

| | | | |
|---|---|---|---|
| 2012/0065492 A1* | 3/2012 | Gertner | A61B 5/201 600/411 |
| 2013/0035682 A1* | 2/2013 | Weil | A61N 5/103 606/33 |
| 2013/0123778 A1* | 5/2013 | Richardson | A61B 18/1492 606/41 |
| 2013/0178824 A1* | 7/2013 | Buelna | A61B 18/00 604/506 |

* cited by examiner

APPLICATION OF RADIOFREQUENCY CATHETER ABLATION SYSTEM TO TREATMENT OF ESSENTIAL HYPERTENSION

TECHNICAL FIELD

The present invention belongs to the field of hypertension treatment, and particularly relates to application of a radiofrequency catheter ablation system to treatment of essential hypertension.

RELATED ART

The effect of radiofrequency catheter ablation for treating primary tumors unable to be treated through surgery, and primary tumors on which radiotherapy and chemotherapy effects are poor has been approved by medical fraternity both in China and abroad. A thermal ablation lesion generated during treatment is generated by emitting high-frequency current which is about 460 kHz. An electrode needle is made to penetrate into target tissue under ultrasonic guidance, an inner trocar is pushed away, tissue in the electric field of the electrode needle is subjected to ion oscillation and heat generation through friction after electrification, as a result, temperature is increased and can exceed 100° C. (specific temperature can be automatically adjusted and controlled according to setting), and heat can be transmitted to surrounding tissue to generate a spherical ablation lesion, so that a tissue target is dried and solidified till necrosis to realize the treatment effect.

Essential hypertension is one of major chronic diseases endangering human health and life currently, and the incidence rate of the essential hypertension becomes higher and higher as economy develops and the average life span becomes longer. According to the cardiovascular disease report of China in 2006, the number of hypertension patients in China has reached 200 million. It is estimated that by 2025, the hypertension patients across the world will exceed 1.5 billion, including 300 million of Chinese patients.

The essential hypertension can develop from no symptom to organ damage step by step. The awareness rate of patients about the disease is usually low in the stage when no symptom appears. The blood pressure control up-to-standard condition of patients after confirmed diagnosis is still not optimistic. Though both China and America put forward in their own hypertension guides that reducing blood pressure to a normal level as early as possible is the basic requirement of optimizing blood pressure management, it is estimated that the blood pressure control up-to-standard rate of hypertension patients in America is only about 35%, and 8% in China. Therefore, the number of hypertensive complication patients also increases day by day due to the high incidence rate, the low awareness rate and the low control rate of hypertension, and hypertensive complication patients mainly include apoplexy (vascular thrombosis or in situ thrombosis), heart failure (contraction type and relaxation type) and progressive renal failure patients, resulting in great social and economic burden.

Currently, the essential hypertension is mainly treated through long-term oral taking of drugs. There are various kinds of drugs for treating the hypertension, however, the blood pressure level of a large number of patients is still not up to standard. Besides, drug interaction and side effects caused by massive drug taking can affect the decision of a physician on whether treatment continues, or affect the compliance of patients to a treatment scheme. Past studies show that the blood pressure up-to-standard rates of hypertension patients with high, medium and low compliance are 43%, 34% and 33% respectively. The proportion of patients in foreign countries with better compliance to orally taken antihypertensive drugs reaches 50-84%, while only 30% or so in China.

Therefore, it will benefit patients, physicians and a medical system to provide a non-medicine treatment method as replacement therapy. At present, there are mainly two kinds of non-medicine methods for treating hypertension in the world, both of which are invasive. One is transcatheter renal artery sympathetic denervation (RSD), and the other is arteriovenous anastomosis using an ROX device. The principle of RSD is that radiofrequency catheter ablation of renal artery sympathetic nerves is conducted in the hope of breaking off the vicious circle between hypertension and renal damage, so as to reduce blood pressure. A recently released SYMPLICITYIII test result shows that compared with a sham-operated group, the hypertension control proportion and the reduction degree of patients in a transcatheter renal artery sympathetic denervation surgical group do not show obvious statistic difference, indicating that the treatment method is ineffective. The principle of ROX device surgery is that a stable fistula is formed between arteries and veins by means of an interventional method to form left-right diversion at the position of a peripheral blood vessel, so that the capacity of an arterial system is reduced and arterial compliance is improved. The preliminary clinical trial of the device is proved to be remarkably effective, however, no clinical controlled trial of a sham-operated group is conducted yet, and more severe clinical complications, like hematomas, dissection, venous thrombosis, device falling-off and right ventricular volume overload, occur to postoperative patients.

SUMMARY

The present invention aims to provide application of a radiofrequency catheter ablation system to treatment of essential hypertension based on the prior art.

The present invention also aims to provide a method for treating the essential hypertension by means of the radiofrequency catheter ablation system.

The objective of the present invention can be realized through following measures:

according to the application of the radiofrequency catheter ablation system to the treatment of the essential hypertension, a secondary center, discovered by the inventor, for regulating the activity of a whole-body sympathetic system is treated by means of the radiofrequency catheter ablation system, so as to reduce the activity of the whole-body sympathetic system, in this way, the blood pressure level of a hypertension patient can be reduced, side effects caused by oral taking of antihypertensive drugs are avoided, and the risk of cardiovascular complications is reduced.

According to a method for realizing the application, namely the method for treating the essential hypertension by means of the radiofrequency catheter ablation system, under ultrasonic guidance, an electrode needle of the radiofrequency catheter ablation system is made to penetrate into one side of perirenal fat tissue of an essential hypertension patient, electrification is conducted to start ablation, the electrode needle is withdrawn and then is made to penetrate into the other side of the perirenal fat tissue of the essential hypertension patient for ablation after reaching ablation temperature and duration time, and the overall ablation range is one third to all of both sides of the perirenal fat tissue till overall ablation treatment is completed; and the target tissue of the ablation treatment is both sides of the perirenal fat tissue.

In the treatment process and method, the target tissue is both sides of the perirenal fat tissue; preferably, the target tissue is both sides of lower perirenal fat tissue, and the preferred target tissue can reduce damage to adjacent tissue (kidney, blood vessels, ureters and other structures) during treatment as much as possible while the treatment purpose is realized.

In one preferred scheme, the target tissue of ablation treatment is both sides of the lower perirenal fat tissue, wherein the lower perirenal fat tissue in the present invention is the fat tissue, located below the lower portion of kidney, in perirenal fat tissue.

In one preferred scheme, the ablation temperature is 40-70° C., particularly 45-60° C., and the duration time is 5-20 seconds, particularly 8-15 seconds.

In one preferred scheme, the overall ablation range is one third to two thirds of both sides of the perirenal fat tissue.

Specifically, the method for treating the essential hypertension by means of the radiofrequency catheter ablation system comprises the following steps of:

(1) before treatment, conducting CT examination on an essential hypertension patient firstly, then conducting ultrasonic multi-section scanning by contrasting with a CT examination result, and measuring the thickness of the target tissue, wherein the target tissue is both sides of the perirenal fat tissue;

(2) establishing a treatment scheme, an ablation mode and ablation procedures according to the illness state of the patient;

(3) conducting sufficient local anaesthesia on the patient from skin to an ablation region (using 1% lidocaine for example);

(4) making the electrode needle of the radiofrequency catheter ablation system penetrate into a locating point in one side of the perirenal fat tissue under ultrasonic guidance, pushing away an inner trocar, and conducting electrification to start ablation;

(5) during ablation, observing the position of the electrode needle in the target tissue by a probe from multiple directions and multiple portions, so as to conduct correction and needle supplement in time;

(6) withdrawing the inner trocar after reaching ablation temperature and time;

(7) conducting ablation of the other side of the perirenal fat tissue according to the treatment scheme by means of the radiofrequency catheter ablation system till overall ablation treatment is completed, wherein the overall ablation range is one third or all of both sides of the perirenal fat tissue; and (8) after treatment, conducting ultrasonic scanning so as to observe or timely find out bad conditions.

In the step (8), whether hydrops and hematocele exist in the perirenal portion and in an abdominal cavity can be observed, so as to find out complications in time.

The application and the method have the advantages that (1) by treating the secondary center, discovered by the inventor, for regulating the activity of the whole-body sympathetic system by means of the radiofrequency catheter ablation system, the activity of the whole-body sympathetic system can be reduced, so that the blood pressure level of an essential hypertension patient can be reduced, and the patient can take fewer kinds and a smaller dosage of antihypertensive drugs or even stop taking the drugs;

(2) by controlling the level of blood pressure and/or blood glucose of the patient, the risk of cardiovascular complications is reduced; and (3) by treating the secondary center, the activity of the whole-body sympathetic system is reduced, insulin resistance is reduced, whole-body fibrosis is reduced, and other diseases, such as sudden cardiac death, ventricular arrhythmias of various types and heart failure, characterized in activity abnormity of the sympathetic system might be treated too.

DETAILED DESCRIPTION

Figure 1:
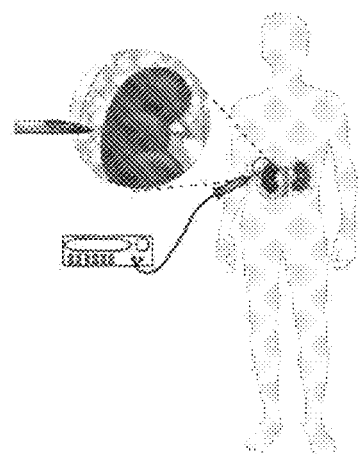
FIG. 1 is a diagram showing how to treat essential hypertension by means of a radiofrequency catheter ablation system according to the present invention.

Further explanation is made with reference to the drawings and embodiments, however, the protection scope of the prevent invention is not limited to the embodiments.

Embodiment 1: Treatment of Mild to Moderate Essential Hypertension

Male patient, 45 years old, taking valsartan 80 mg/d before operation, clinical blood pressure being 150/96 mmHg, average blood pressure within 24 h being 145/94 mmHg.

Before treatment, CT examination was conducted on the patient firstly, then ultrasonic multi-section scanning was conducted by contrasting with a CT examination result, and the thickness of lower perirenal fat tissue was measured to be 3.5 cm; sufficient local anaesthesia was conducted on the patient by using 1% lidocaine from skin to an ablation region; an electrode needle of the radiofrequency catheter ablation system was made to penetrate into a locating point in the right side of lower perirenal fat tissue under ultrasonic guidance, an inner trocar was pushed away, electrification was conducted to start ablation, during ablation, the position of the electrode needle in perirenal fat tissue was observed by a probe from multiple directions and multiple portions, so as to conduct correction and needle supplement in time; the inner trocar was withdrawn after local temperature was monitored to reach 55° C. and ablation lasted for 10 seconds; ablation of the other side of the lower perirenal fat tissue was conducted according to the treatment scheme by means of the radiofrequency catheter ablation system till overall ablation treatment was completed, and an overall ablation range was about one third of both sides of the perirenal fat tissue; and after treatment, ultrasonic scanning was conducted to observe the perirenal fat state.

The patients stopped taking antihypertensive drugs after treatment. In one-month follow-up, the clinical blood pressure being 140/90 mmHg, the average blood pressure within 24 h being 136/90 mmHg; in six-month follow-up, the clinical blood pressure being 130/85 mmHg, and the average blood pressure within 24 h being 132/82 mmHg.

Embodiment 2: Treatment of Severe Hypertension

Male patient, 65 years old, taking nifedipine controlled release tablets 90 mg/d, valsartan 80 mg/d, hydrochlorothiazide 12.5 mg/d, metoprolol sustained-release tablets 95 mg/d, spirolactone 20 mg/d and terazosin 2 mg/d before operation, clinical blood pressure being 160/105 mmHg, average blood pressure within 24 h being 150/97 mmHg.

Before treatment, CT examination was conducted on the patient firstly, then ultrasonic multi-section scanning was conducted by contrasting with a CT examination result, and the thickness of lower perirenal fat tissue was measured to be 5.9 cm; sufficient local anaesthesia was conducted on the patient by using 1% lidocaine from skin to an ablation region; an electrode needle of the radiofrequency catheter ablation system was made to penetrate into a locating point in the right side of lower perirenal fat tissue under ultrasonic guidance, an inner trocar was pushed away, electrification was conducted to start ablation, during ablation, the position of the electrode needle in the perirenal fat tissue was observed by a probe from multiple directions and multiple portions, so as to conduct correction and needle supplement in time; the inner trocar was withdrawn after local temperature was monitored to reach 60° C. and ablation lasted for 10 seconds; ablation of the other side of the lower perirenal fat tissue was conducted according to the treatment scheme by means of the radiofrequency catheter ablation system till overall ablation treatment was completed, and an overall ablation range was about two thirds of both sides of the perirenal fat tissue; and after treatment, ultrasonic scanning was conducted to observe the perirenal fat state.

After treatment, the patient only took nifedipine controlled release tablets 30 mg/d, irbesartan 150 mg/d and metoprolol tablets 25 mg/d. In one-month follow-up, the clinical blood pressure being 135/90 mmHg, the average blood pressure within 24 h being 128/87 mmHg; in six-month follow-up, the clinical blood pressure being 135/88 mmHg, and the average blood pressure within 24 h being 130/85 mmHg.

Embodiment 3: Animal and Human Trials

We have conducted 30 animal trials and 10 human trials.

Figure 2:
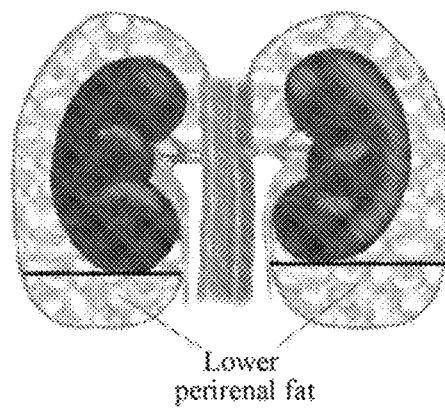
FIG. 2 is a diagram of lower perirenal fat tissue.
Figure 3:
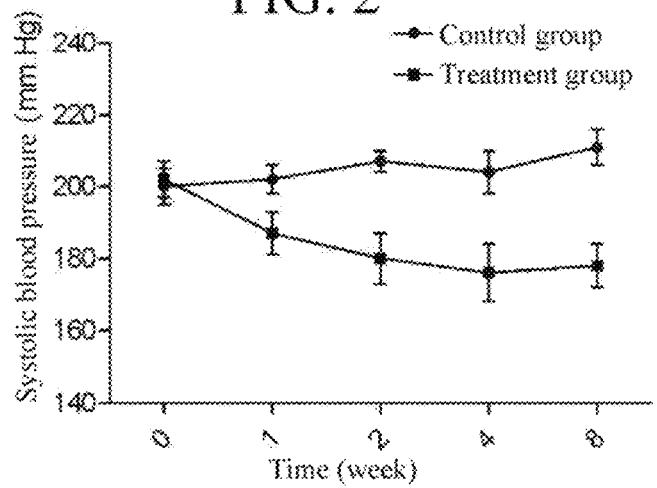
FIG. 3 is a diagram showing the influence of the radiofrequency catheter ablation system on the blood pressure of a hypertension model SD rat by damaging perirenal fat tissue.

In the animal trials, an electrode needle of the radiofrequency catheter ablation system was made to penetrate into lower perirenal fat tissue of a hypertension model SD rat under ultrasonic guidance, electrification was conducted to start ablation, the electrode needle was withdrawn after ablation temperature reached 55° C. and ablation lasted for 10 seconds, then the electrode needle was made to penetrate into the other side of the lower perirenal fat tissue for target ablation till overall ablation therapy was completed, and an overall ablation range was about half of both sides of perirenal fat tissue. The animal trials suggest that after specific treatment was conducted on the hypertension model animal (SD rat), blood pressure dropped to a normal range about one week after surgery, the blood pressure stayed in a normal and steady state during 8-week follow-up, and no blood pressure rebound situation was occurred (FIG. 2).

The 10 preliminary human trials included refractory hypertension, and hypertension patients accompanied by cardio-cerebrovascular complications.

Specific target measurement and local anesthesia processes are like embodiment 1 and embodiment 2, and an ablation process is that an electrode needle of the radiofrequency catheter ablation system was made to penetrate into lower perirenal fat tissue of an essential hypertension patient under ultrasonic guidance, electrification was conducted to start ablation, the electrode needle was withdrawn after ablation temperature reached 55° C. and ablation lasted for 10 seconds, then the electrode needle was made to penetrate into the other side of the lower perirenal fat tissue for target ablation till overall ablation therapy was completed, and the overall ablation range was one third to all of both sides of perirenal fat tissue.

The blood pressure of all the patients dropped steadily without exception after surgery, the patients took fewer kinds and a smaller dosage of antihypertensive drugs, and three patients can even stop taking the drugs. Now we have conducted follow-up for over 6 months and found that the blood pressure of the patients is steady, and no rebound situation occurred.

What is claimed is:

1. Application of a radiofrequency catheter ablation system to treatment of essential hypertension, wherein
    under ultrasonic guidance, an electrode needle of the radiofrequency catheter ablation system is made to penetrate into one side of perirenal fat tissue of an essential hypertension patient, and electrification is conducted to start ablation,
    after reaching ablation temperature and duration time, the electrode needle is withdrawn and then is made to penetrate into the other side of the perirenal fat tissue for ablation until an overall ablation treatment is completed when an overall ablation range is one third to all of both sides of the perirenal fat tissue, and
    a target tissue of the ablation treatment is both sides of the perirenal fat tissue.

2. The application according to claim 1, wherein the target tissue is both sides of lower perirenal fat tissue.

3. The application according to claim 1, wherein the ablation temperature is 40-70° C. and the duration time is 5-20 seconds.

4. The application according to claim 3, wherein the ablation temperature is 45-60° C. and the duration time is 8-15 seconds.

5. The application according to claim 1, wherein the overall ablation treatment is completed when the overall ablation range is one third to two thirds of both sides of the perirenal fat tissue.

6. The application according to claim 1, wherein:
    before treatment, CT examination is conducted on the patient firstly, then ultrasonic multi-section scanning is conducted by contrasting with a CT examination result, and a thickness of the target tissue is measured;
    a treatment scheme, an ablation mode and ablation procedures are established according to an illness state of the patient, and sufficient local anaesthesia is conducted on the patient from skin to an ablation region;
    the application of the radiofrequency catheter ablation system of claim 2 is performed with the proviso that:
        the electrode needle of the radiofrequency catheter ablation system of claim 2 is made to penetrate into one side of the perirenal fat tissue under ultrasonic guidance, an inner trocar is pushed away, electrification is conducted to start ablation, during ablation, a position of the electrode needle in the perirenal fat tissue is observed by a probe from multiple directions and multiple portions, so as to conduct correction and needle supplement in time;
        the inner trocar is withdrawn after reaching the ablation temperature of 40-70° C. and the duration time;
        ablation of the other side of the perirenal fat tissue of the target tissue is conducted according to the treatment scheme until the overall ablation treatment is completed; and after the ablation treatment, ultrasonic scanning is conducted so as to observe or timely find out bad conditions.

7. The application according to claim 6, wherein the target tissue is both sides of lower perirenal fat tissue.

8. The application according to claim 6, wherein the ablation temperature is 40-70° C., and the duration time is 5-20 seconds.

9. The application according to claim 8, wherein the ablation temperature is 45-60° C., and the duration time is 8-15 seconds.

10. The application according to claim 6, wherein the overall ablation treatment is completed when the overall ablation range is one third to two thirds of both sides of the perirenal fat tissue.

11. A method for treating essential hypertension by means of a radiofrequency catheter ablation system, wherein
under ultrasonic guidance, an electrode needle of the radiofrequency catheter ablation system is made to penetrate into one side of perirenal fat tissue of an essential hypertension patient, and electrification is conducted to start ablation,
after reaching ablation temperature and duration time, the electrode needle is withdrawn or is made to penetrate into the other side of the perirenal fat tissue for ablation until an overall ablation treatment is completed when an overall ablation range is one third to all of both sides of the perirenal fat tissue, and
a target tissue of the ablation treatment is both sides of the perirenal fat tissue.

12. The method according to claim 11, comprising the following steps of:
(1) before treatment, conducting CT examination on an essential hypertension patient firstly, then conducting ultrasonic multi-section scanning by contrasting with a CT examination result, and measuring a thickness of the target tissue;
(2) establishing a treatment scheme, an ablation mode and ablation procedures according to an illness state of the patient;
(3) conducting sufficient local anaesthesia on the patient from skin to an ablation region;
(4) making the electrode needle of the radiofrequency catheter ablation system of claim 7 penetrate into a locating point in one side of the perirenal fat tissue under ultrasonic guidance, pushing away an inner trocar, and conducting electrification to start ablation;
(5) during ablation, observing a position of the electrode needle in the perirenal fat tissue by a probe from multiple directions and multiple portions, so as to conduct correction and needle supplement in time;
(6) withdrawing the inner trocar after reaching the ablation temperature and the duration time;
(7) conducting ablation of the other side of the perirenal fat tissue by means of the radiofrequency catheter ablation system of claim 7 according to the treatment scheme, until the overall ablation treatment is completed; and
(8) after the ablation treatment, conducting ultrasonic scanning so as to observe or timely find out bad conditions.

13. The method according to claim 12, wherein the target tissue is both sides of lower perirenal fat tissue.

14. The method according to claim 12, wherein the overall ablation treatment is completed when the overall ablation range is one third to two thirds of both sides of the perirenal fat tissue.

15. The method according to claim 12, wherein the ablation temperature is 40-70° C. and the duration time is 5-20 seconds.

16. The method according to claim 15, wherein the ablation temperature is 45-60° C. and the duration time is 8-15 seconds.

17. The method according to claim 11, wherein the target tissue is both sides of lower perirenal fat tissue.

18. The method according to claim 11, wherein the ablation temperature is 40-70° C. and the duration time is 5-20 seconds.

19. The method according to claim 18, wherein the ablation temperature is 45-60° C. and the duration time is 8-15 seconds.

20. The method according to claim 11, wherein the overall ablation treatment is completed when the overall ablation range is one third to two thirds of both sides of the perirenal fat tissue.

* * * * *